(12) United States Patent
Kawase

(10) Patent No.: US 6,420,624 B1
(45) Date of Patent: Jul. 16, 2002

(54) BLOOD CIRCULATION-PROMOTING POWDERY MATERIAL, BLOOD CIRCULATION-PROMOTING ATTACHMENT SHEET AND BLOOD CIRCULATION-PROMOTING ATTACHMENT SHEET SET

(75) Inventor: Ituko Kawase, Fujinomiya (JP)

(73) Assignee: Hanakobosanphan Co. Ltd., Shizuoka-ken (JP)

( * ) Notice: Subject to any disclaimer, the term of this patent is extended or adjusted under 35 U.S.C. 154(b) by 119 days.

(21) Appl. No.: 09/617,696

(22) Filed: Jul. 17, 2000

(30) Foreign Application Priority Data

Jul. 22, 1999 (JP) ............................ 11-005455
Jul. 22, 1999 (JP) ............................ 11-207184

(51) Int. Cl.$^7$ ................................ A61F 13/00
(52) U.S. Cl. ........................ 602/48; 602/54; 604/304
(58) Field of Search ............ 602/41–59; 604/304–308; 128/888, 889; 424/443–448

(56) References Cited

U.S. PATENT DOCUMENTS 5,024,731 A * 6/1991 Nagata et al. ................ 203/99

* cited by examiner

*Primary Examiner*—Kim M. Lewis
(74) *Attorney, Agent, or Firm*—Price and Gess

(57) ABSTRACT

A blood circulation-promoting powdery material, a blood circulation-promoting attachment sheet and a blood circulation-promoting attachment sheet set for promoting blood circulation is provided. The powdery material comprises a distillate recovered from the distillation of pyroligneous acid as the principal component. The blood circulation-promoting attachment sheet includes the powdery material placed in a bag-shape sheet with air permeability; and the blood circulation-promoting attachment sheet set includes a bag-shape sheet containing the powdery material with an adhesive material and air permeability provided on one face of the attachment sheet.

20 Claims, 2 Drawing Sheets

BLOOD CIRCULATION-PROMOTING POWDERY MATERIAL, BLOOD CIRCULATION-PROMOTING ATTACHMENT SHEET AND BLOOD CIRCULATION-PROMOTING ATTACHMENT SHEET SET

BACKGROUND OF THE INVENTION

1. Field of the Invention

The present invention relates to a blood circulation-promoting attachment sheet for use in the attached form on foot sole, leg ankle, knee and the like, and a blood circulation-promoting attachment sheet set therefor.

2. Description of the Related Art

Because humans move and make actions on two legs, fatigue and waste products are retained in the legs supporting the bodies, so that edema and fatigue sometimes occur in the legs, leading to the emergence of the bodies out of condition. Therefore, methods for controlling health, such as stamping on bamboo shoot chop arranged flat on floor and meridian pushing, are widely distributed, so as to stimulate meridian spots in the leg region. and thereby promote systemic blood circulation to propagate the excretion of waste products out of the bodies.

Alternatively, blood circulation is also promoted by the actions of the effective components contained in commercially available cataplasmata products attached on foot sole, leg ankle, knee and the like, but materials are needed, which are capable of more efficiently giving an effect on the promotion of blood circulation to reduce the feeling of fatigue and various aches and pains.

SUMMARY OF THE INVENTION

The invention has been proposed to satisfy such need. The invention relates to a blood circulation-promoting powdery material, a blood circulation-promoting attachment sheet and a blood circulation-promoting attachment sheet set, all of which can efficiently give a blood circulation-promoting effect and thereby reduce the feeling of fatigue and various aches and pains.

The inventor has made various investigations. Consequently, the inventor has found that a powdery material containing as the principal component a distillate of 95 to 105° C. recovered from the distillation of pyroligneous acid exerts its action on a foot sole and the like, to promote blood circulation with consequent effects on the reduction of the feeling of fatigue and the reduction of aches and pains caused by rheumatoid and the like.

DETAILED DESCRIPTION OF THE INVENTION

Figure 1:
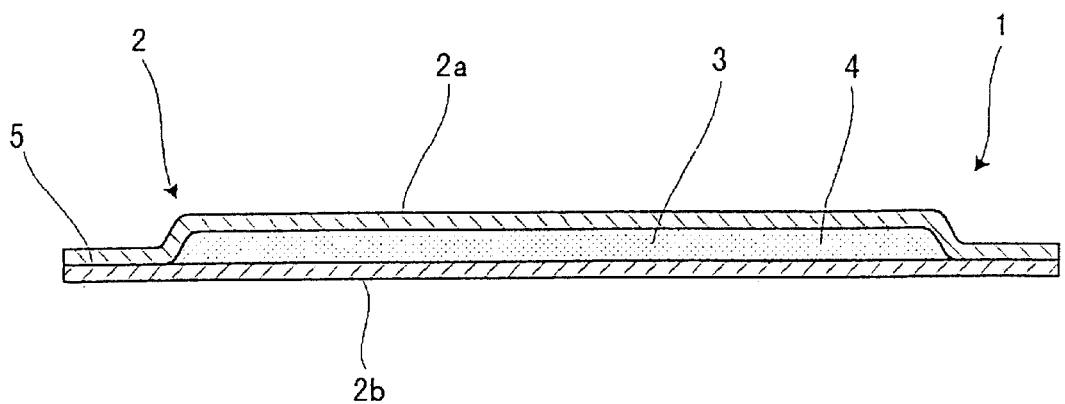
FIG. 1 is a cross sectional view depicting one example of the blood circulation-promoting attachment sheet for use in accordance with the invention.

The pyroligneous acid as a subject in accordance with the invention is in the form of an aqueous solution prepared by carbonizing plants such as tree bark, tree and bamboo and cooling the fume then generated; and the pyroligneous acid contains chemical components, varying depending on the type of a raw material to be carbonized but typically including acetic acid, propionic acid, butyric acid, methanol, formaldehyde, phenol, furfural, cresol and creosol.

The pyroligneous acid contains tannins (for example, phenol as one component) repairing dermal damage and increasing moisture but concomitantly contains biologically hazardous components such as formaldehyde and methanol at several hundreds in ppm, which are serious drawbacks for the use of pyroligneous acid as it is as cosmetics and medicinal products.

In accordance with the invention, the biologically hazardous components (formaldehyde, methanol, etc.) in pyroligneous acid are removed by the distillation of pyroligneous acid, so that high-quality pyroligneous acid containing effective components such as flavanol, tannin, polyphenol, cresol and creosol is recovered; and the resulting pyroligneous acid is thereafter modified into a powdery material. In such manner, a blood circulation-promoting attachment sheet can be prepared for use on humans with great safety.

The inventor has found that a distillate of 95 to 105° C. recovered from the distillation of pyroligneous acid, from which low boiling distillates have been removed and which never contains any high boiling distillates, promotes blood circulation and has an effect on the absorption of excess moisture on a part attached therewith; that simply dried and pulverized pyroligneous acid has very strong smell of acetic acid but the powdery material containing the distillate of 95 to 105° C. as the principal component has less odor of acetic acid with less problems for use, although pyroligneous acid has conventionally been used widely as deodorant; and that the powdery material in combination with one or two or more of plant essence oils or plant extracts can particularly enhance the effect.

The reason why the distillate promotes blood circulation with an effect on the reduction of the feeling of fatigue is not necessarily elucidated, but it is considered that the distillate absorbs excessive moisture (possibly, unnecessary lymphatic fluid oozed out of blood tube) in bodies and allows toxins in bodies [due to so-called disorders of the metabolism of fluid excretion (shui du)] to be excreted, so that the circulation of blood and lymphatic fluid in retention in bodies is controlled with an effect on the elevation of blood flow.

In this case, additionally, the powdery material can directly exert its action on foot sole, leg ankle, knee and the like through the air-permeable pores of a bag-shape sheet containing the powdery material and simultaneously draws out and absorbs excessive moisture on a site attached with the sheet through the air-permeable pores in a secure manner. Hence, the effect of the powdery material can be exerted efficiently owing to the sheet form, compared with conventional cataplasmata comprising effective components contained in base materials in emulsion for use in the form with no practical moisture absorptivity.

Because the air-permeable face of the bag-shape sheet is not adhesive enough to be attached on foot sole and the like, furthermore, an adhesive sheet at a dimension larger than that of the bag-shape sheet is alternatively prepared, by using non-woven fabric or woven fabric or the like to preferably give elasticity in lengthwise and crosswise directions to the adhesive sheet and to additionally give air permeability thereto and then depositing an adhesive on one face thereof to give adhesiveness to the material of the adhesive sheet; by subsequently placing and attaching the non-air-permeable face (or the opposite face to the face to be attached on foot sole and the like) of the bag-shape sheet on the one adhesive face and then attaching the adhesive sheet on foot sole and the like, the powdery material charged in the bag-shape sheet can be applied to a lesion in a secure manner.

DESCRIPTION OF THE PREFERRED EMBODIMENT

The invention will now be described in more detail in the following examples.

EXAMPLE

Figure 2:
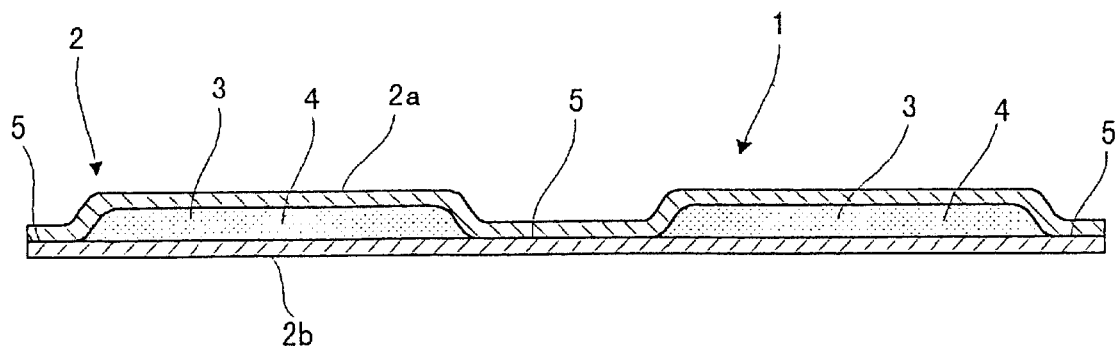
FIG. 2 is a cross sectional view depicting another example of the blood circulation-promoting attachment sheet for use in accordance with the invention.

FIG. 1 depicts one example of the invention, wherein 1 represents blood circulation-promoting attachment sheet comprising bag-shape sheet 2 comprising air-permeable sheet 2a on one face and non-air-permeable sheet 2b on the other face and placing powdery material 4 in a small chamber 3 thereof. Herein, the symbol 5 in the figure represents an attachment part of both the sheets 2a, 2b by means of adhesion and fusion. Additionally, FIG. 2 depicts two such bag-shape sheets 2, 2 connected through the attachment part 5 together, which can be cut and separated at the attachment part 5 on use.

The bag-shape sheet 2 is not limited to the illustrated examples but can be prepared for example by folding one air-permeable sheet together and bonding the resulting end parts thereof together. The bag-shape sheet 2 can be made of materials such as woven fabric, non-woven fabric, paper and plastic sheet, but as described above, at least one face of the bag-shape sheet 2 is air permeable and is preferably made of a material with air permeability without any leakage of the powdery material, such as Japanese traditional paper called washi, while the other face thereof is made of a non-air-permeable sheet.

The bag-shape sheet 2 is of a dimension attachable and applicable to the foot sole, leg ankle, knee and the like and as described above, plural such sheets are connected together and can be cut out one by one on use.

The air-permeable face of the bag-shape sheet 2 corresponds to the attachment face on foot sole and the like, but if necessary, a release sheet satisfactorily is attached on the air-permeable face in a releasable fashion and is then released on use.

Figure 3:
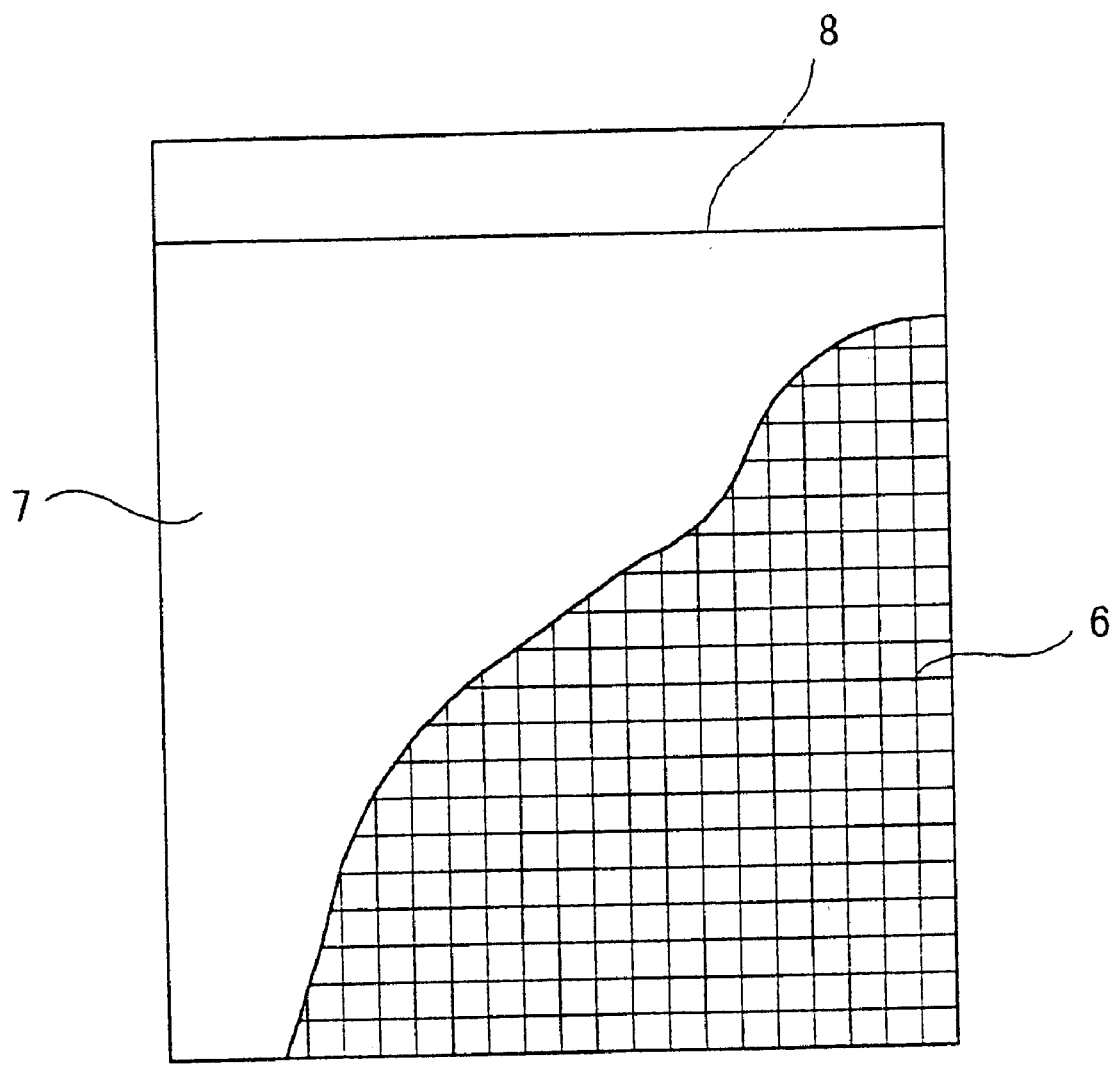
FIG. 3 is a partially notched plan view depicting one example of an adhesive sheet for use in accordance with the invention.

FIG. 3 depicts on example of adhesive sheet 6. The adhesive sheet 6 is prepared at a dimension larger than that of the bag-shape sheet 2, by using a sheet with air permeability and elasticity in lengthwise and crosswise directions, such as woven fabric and non-woven fabric; and additionally, one face thereof is preliminarily treated at an adhesive deposition process so as to give adhesiveness to the one face. Release sheet 7 such as release paper is further attached in a releasable manner on the adhesive face. The symbol 8 represents a cut portion. The release sheet 7 can be separated and released upward and downward at the cut portion 8.

Not shown in the figure, additionally, plural sheets of each of the bag-shape sheet 2 and the adhesive sheet 6 are preferably placed in a non-air-permeable bag.

As the powdery material promoting blood circulation with an effect on the reduction of the feeling of fatigue and aches and pains, the following materials are used as described above.

1. A powdery material prepared by distilling pyroligneous acid and recovering a distillate at 95 to 105° C., particularly at 98 to 103° C. and pulverizing the resulting distillate by spray drying, freeze drying and the like.
2. The distillate adsorbed and immobilized on a powdery carrier comprising for example cyclodextrin, starch, a powder of cereals and potatoes such as corn, potato and sweet potato, silica and active charcoal.
3. A product prepared by removing moisture from the distillate, melting the resulting distillate at a temperature of about 200° C. and spraying, adsorbing or immobilizing the resulting melted material on the powdery carrier.

In accordance with the invention, it is recommended that one or two or more of plant essence oils or plant extracts are used in combination with the powdery material. In this case, the plant essence oils or plant extracts include for example those recovered from garlic, anise, basil, bergamot, chamomile, cinnamon, caraway, lemon, coriander, eucalyptus, fennel, geranium, ginger, beefsteak plant (*Perilla frutescens* crispa), clove, lavender, marjoram, peppermint, spearmint, nutmeg, onion, orange, pine, rosemary, sage, thyme, turpentine, German chamomile, saffron, melissa, mint, artichoke, Kalmus, clove, cinnamon bark, elder berry, anisi stellati fructus, cnidium rhizome, Japanese angelica root, Salvia officinalis, western milfoil, and horse chestnut marronnier. These can be used singly or in combination of two or more thereof. By using the combination of these essence oils and extracts, the slight acetic acid odor still remaining in the distillate of pyroligneous acid can be masked, while the pharmacological efficacy of the essence oils and the extracts can be procured.

These essence oils and extracts can be blended in total at 0.05 to 10 parts by weight, particularly about 0.1 to 5 parts by weight per 100 parts by weight of the powdery material, with no limitation. The quantity thereof to be blended can appropriately be selected.

The blood circulation-promoting attachment sheet set comprises a combination of the bag-shape sheet placing the powdery material therein and the adhesive sheet. For use, the release sheet is released from the adhesive sheet; the opposite face to the attachment face of the bag-shape sheet on foot sole and the like is placed on the adhesive face to attach the bag-shape sheet thereon; and the adhesive sheet is then attached on a lesion of foot sole, leg ankle, knee and the like, while the attachment face of the bag-shape sheet is faced toward the lesion. In such manner, the action of the powdery material can promote blood circulation and reduce fatigue, and during the exertion of the action, the powdery material of the bag-shape sheet can draw out and absorb excessive moisture of lesions on for example a foot sole, through the air-permeable pores of the sheet.

Experimental Example

By distilling pyroligneous acid, a distillate of 98 to 103° C. was recovered while distillates at 98° C. or less were discarded. The distillate was cooled to prepare a fluid material. From the fluid material was removed about 90% of the moisture; and the resulting material was melted at about 200° C. and was then adsorbed and immobilized on cyclodextrin by spraying, to recover a powdery material. To the powdery material was added a small amount of a mixture of several-tens types of the essence oils and the extracts; the resulting powdery material was charged in the bag-shape sheet depicted in FIG. 1, to prepare a blood circulation-promoting attachment sheet.

The blood circulation-promoting attachment sheet was attached on and applied to the foot soles of several users with accumulated fatigue, prior to sleep. On the next morning, the sheet was peeled off, for observation of the state of the powdery material in the sheet. Consequently, the powdery material from each of the users was considerably moistened at a state colored yellow to brown. After the application was continued for several days, consequently, all the test subjects replied that their fatigue was reduced, while some replied that the dullness in their calves, in particular, disappeared and the aches and pains in their knees were prominently reduced.

The blood circulation-promoting attachment sheet was alternatively applied on the aching lesions of the foot soles, leg ankles, knees and hand wrists of rheumatoid patients. Consequently, the powdery material was colored yellowish earth color in about 10 minutes, involving the emergence of bad smell. The patients replied after the application thereof on the foot soles for several days that their pains were reduced.

The blood circulation-promoting attachment sheet was additionally applied to the foot sole and knee of a patient with water retention in the knee with pain. In two hours, the powdery material was colored brown and moistened at a significant degree due to the moisture, involving the emergence of bad smell. After subsequent one-month application thereof while the bag-shape sheet was exchanged to a fresh one every day, consequently, the patient replied that the powdery material took a longer time until the powdery material was moistened and that the pain was fairly reduced.

As described above insofar, a blood circulation-promoting powdery material, a blood circulation-promoting attachment sheet and a blood circulation-promoting sheet set can be provided in accordance with the invention, all of which are of good applicability in case that these are used in the attached forms on foot sole, leg ankle, knee and the like and function for promoting blood circulation to thereby reduce the feeling of fatigue.

What is claimed is:

1. A blood circulation-promoting powdery material comprising:
   a distillate of 95 to 105° C. recovered from the distillation of pyroligneous acid as the principal component.

2. The blood circulation-promoting powdery material according to claim 1, wherein the powdery material is prepared by recovering the distillate of pyroligneous acid and pulverizing the distillate by spray drying or freeze drying.

3. The blood circulation-promoting powdery material according to claim 1, wherein the powdery material is prepared by immobilizing the distillate of pyroligneous acid on a powdery carrier comprising one or more selected from cyclodextrin, starch, powders of cereals and potatoes, silica and active charcoal.

4. The blood circulation-promoting powdery material according to claim 1, wherein the powdery material is prepared by removing moisture from the distillate of pyroligneous acid, then melting the resulting distillate at a temperature of about 200° C. and spraying, adsorbing or immobilizing the resulting melted distillate on a powdery carrier comprising one or more selected from cyclodextrin, starch, powders of cereals and potatoes, silica and active charcoal.

5. The blood circulation-promoting powdery material according to claim 1, wherein the powdery material comprises a mixture of plant essence oils or plant extracts.

6. The blood circulation-promoting powdery material according to claim 5, wherein the plant essence oils or plant extracts comprise any one from a plant essence oil or plant extract recovered from garlic, anise, basil, bergamot, chamomile, cinnamon, caraway, lemon, coriander, eucalyptus, fennel, geranium, ginger, beefsteak plant (*Perilla frutescens* crispa), clove, lavender, marjoram, peppermint, spearmint, nutmeg, onion, orange, pine, rosemary, sage, thyme, turpentine, German chamomile, saffron, melissa, mint, artichoke, Kalmus, clove, cinnamon bark, elder berry, anisi stellati fructus, cnidium rhizome, Japanese angelica root, Salvia officinalis, Western milfoil, and horse chestnut marronier, or a combination of plural such plant essence oils or plant extracts.

7. A blood circulation-promoting attachment sheet comprising a powdery material containing a distillate of 95 to 105° C. recovered from the distillation of pyroligneous acid as the principal component, as placed in a bag-shape sheet with air permeability.

8. The blood circulation-promoting attachment sheet according to claim 7, wherein the powdery material is prepared by recovering the distillate of pyroligneous acid and pulverizing the distillate by spray drying or freeze drying.

9. The blood circulation-promoting attachment sheet according to claim 7, wherein the powdery material is prepared by immobilizing the distillate of pyroligneous acid on a powdery carrier comprising one or more selected from cyclodextrin, starch, powders of cereals and potatoes, silica and active charcoal.

10. The blood circulation-promoting attachment sheet according to claim 7, wherein the powdery material is prepared by removing moisture from the distillate of pyroligneous acid, then melting the resulting distillate at a temperature of about 200° C. and spraying, adsorbing or immobilizing the resulting melted distillate on a powdery carrier comprising one or more selected from cyclodextrin, starch, powders of cereals and potatoes, silica and active charcoal.

11. The blood circulation-promoting attachment sheet according to claim 7, wherein the powdery material comprises a mixture of plant essence oils or plant extracts.

12. The blood circulation-promoting attachment sheet according to claim 11, wherein the plant essence oils or plant extracts comprise any one plant essence oil or plant extract recovered from garlic, anise, basil, bergamot, chamomile, cinnamon, caraway, lemon, coriander, eucalyptus, fennel, geranium, ginger, beefsteak plant (*Perilla frutescens* crispa), clove, lavender, marjoram, peppermint, spearmint, nutmeg, onion, orange, pine, rosemary, sage, thyme, turpentine, German chamomile, saffron, melissa, mint, artichoke, Kalmus, clove, cinnamon bark, elder berry, anisi stellati fructus, cnidium rhizome, Japanese angelica root, Salvia officinalis, Western milfoil, and horse chestnut marronnier, or a combination of plural such plant essence oils or plant extracts.

13. A blood circulation-promoting attachment sheet set, comprising:
   a bag-shape sheet being air permeable on at least one face thereof and having therein a powdery material containing a distillate of 95 to 105° C. recovered from the distillation of pyroligneous acid as the principal component; and
   an adhesive sheet at a dimension larger than that of the bag-shape sheet and with adhesiveness and air permeability on one face thereof.

14. The blood circulation-promoting attachment sheet set according to claim 13, wherein the powdery material is prepared by recovering the distillate of pyroligneous acid and pulverizing the distillate by spray drying or freeze drying.

15. The blood circulation-promoting attachment sheet set according to claim 13, wherein the powdery material is prepared by immobilizing the distillate of pyroligneous acid on a powdery carrier comprising one or more selected from cyclodextrin, starch, powders of cereals and potatoes, silica and active charcoal.

16. The blood circulation-promoting attachment sheet set according to claim 13, wherein the powdery material is prepared by removing moisture from the distillate of pyroligneous acid, then melting the resulting distillate at a temperature of about 200° C. and spraying, adsorbing or immobilizing the resulting melted distillate on a powdery carrier comprising one or more selected from cyclodextrin, starch, powders of cereals and potatoes, silica and active charcoal.

17. The blood circulation-promoting attachment sheet set according to claim 13, wherein the powdery material comprises a mixture of plant essence oils or plant extracts.

18. The blood circulation-promoting attachment sheet set according to claim 17, wherein the plant essence oils or plant extracts comprise any one plant essence oil or plant extract recovered from garlic, anise, basil, bergamot, chamomile, cinnamon, caraway, lemon, coriander, eucalyptus, fennel, geranium, ginger, beefsteak plant (*Perilla frutescens* crispa), clove, lavender, marjoram, peppermint, spearmint, nutmeg, onion, orange, pine, rosemary, sage, thyme, turpentine, German chamomile, saffron, melissa, mint, artichoke, Kalmus, clove, cinnamon bark, elder berry, anisi stellati fructus, cnidium rhizome, Japanese angelica root, Salvia officinalis, Western milfoil, and horse chestnut marronnier, or a combination of plural such plant essence oils or plant extracts.

19. A method of promoting blood circulation in a user, comprising the steps of:

preparing a distillate of pyroligneous acid, the distillate recovered from heating the pyroligneous acid within a temperature range of 95° C. to 105° C.;

drying the distillate into a powder form;

encompassing the powder into a porous flexible dressing; and applying the dressing to a desired area of treatment on the user.

20. The method of claim 19 wherein the powder includes a carrier material and an aromatic additive.

* * * * *